(12) United States Patent
Honda

(10) Patent No.: US 10,687,835 B2
(45) Date of Patent: Jun. 23, 2020

(54) CALCULUS REMOVING DEVICE

(71) Applicant: TERUMO KABUSHIKI KAISHA, Shibuya-ku, Tokyo (JP)

(72) Inventor: Kei Honda, Hadano (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 589 days.

(21) Appl. No.: 14/858,537

(22) Filed: Sep. 18, 2015

(65) Prior Publication Data
US 2016/0081701 A1    Mar. 24, 2016

(30) Foreign Application Priority Data

Sep. 19, 2014  (JP) ................................ 2014-191788

(51) Int. Cl.
*A61B 17/221* (2006.01)
*A61B 10/02* (2006.01)

(52) U.S. Cl.
CPC .... *A61B 17/221* (2013.01); *A61B 2010/0225* (2013.01); *A61B 2017/2215* (2013.01); *A61B 2017/2217* (2013.01)

(58) Field of Classification Search
CPC .......... A61B 17/221; A61B 2017/2215; A61B 2017/2217
See application file for complete search history.

(56) References Cited

U.S. PATENT DOCUMENTS

| | | | | |
|---|---|---|---|---|
| 7,285,126 | B2 * | 10/2007 | Sepetka | A61B 17/22031 606/113 |
| 2008/0045881 | A1 * | 2/2008 | Teitelbaum | A61B 17/22031 604/21 |
| 2010/0016792 | A1 * | 1/2010 | Hirszowicz | A61B 17/22031 604/96.01 |

(Continued)

FOREIGN PATENT DOCUMENTS

| | | |
|---|---|---|
| DE | 10 2010 014 778 A1 | 10/2011 |
| JP | H11-047140 A | 2/1999 |
| JP | 2001-512355 A | 8/2001 |

(Continued)

OTHER PUBLICATIONS

An English Translation of the Japanese Office Action (Notification of Reasons for Refusal) dated May 22, 2018, by the Japanese Patent Office in corresponding Japanese Patent Application No. 2014-191788. (3 pages).

*Primary Examiner* — Sarah A Simpson
(74) *Attorney, Agent, or Firm* — Buchanan Ingersoll & Rooney PC

(57) ABSTRACT

A calculus removing device includes a retaining portion (e.g., a wire or gel), a cylinder, an introduction tube, and a hand-operated unit. The retaining portion is configured to retain calculi and broken calculus pieces. The cylinder includes a storage portion configured to store the calculi, an opening communicating with the storage portion, and an introducing portion configured to permit the retaining portion to be introduced into the storage portion. The introduc- (Continued)

tion tube is provided with a lumen which allows introduction of the retaining portion into the storage portion via the introducing portion. The hand operating unit is provided with an operating member configured to operate the introduction of the retaining portion into the storage portion.

18 Claims, 9 Drawing Sheets

(56) References Cited

U.S. PATENT DOCUMENTS

2010/0036312 A1* 2/2010 Krolik ............... A61B 17/221
       604/22
2011/0295305 A1* 12/2011 Morero ............. A61B 17/221
       606/200

FOREIGN PATENT DOCUMENTS

| JP | 2010-213918 A | 9/2010 |
| JP | 2011-522635 A | 8/2011 |
| WO | WO 99/36694 A1 | 8/1998 |

* cited by examiner

CALCULUS REMOVING DEVICE

CROSS-REFERENCES TO RELATED APPLICATIONS

This application claims priority to Japanese Application No. 2014-191788 filed on Sep. 19, 2014, the entire content of which is incorporated herein by reference.

TECHNICAL FIELD

The present invention generally relates to a calculus removing device.

BACKGROUND DISCUSSION

Urinary stones include stones existing in a urinary tract such as a kidney, a ureter, a bladder, a urethra, and the like, and a calculus generated in a kidney or in a ureter is referred to as an upper urinary stone. In urinary tract stone disease, various symptomatic states are caused by these urinary stones. For example, in the case where a calculus generated in a kidney is moved to a ureter, the calculus damages the ureter and causes a pain in the urine, or the calculus blocks the ureter, so that a transient hydronephrosis state is generated, and hence an acute pain (colic pain) from a lower back to a lateral region may result. In order to alleviate or treat these symptoms, removal of the calculus is effective means.

In the urinary tract stone disease, if effects such as natural stone drainage and a conservative medical treatment cannot be expected, a surgical positive removal method is performed. Examples of the positive removal method include mainly an Extracorporeal Shock Wave Lithotripsy (ESWL), a Transurethral Resection of Lithotripsy (TUL or URS), and Percutaneous Nephrolithotripsy (PNL or PCNL). Examples of the TUL include an r-TUL (or r-URS) in which a hard renal pelvis ureter mirror (hereinafter, referred to as a hard mirror) is used, and an f-TUL (or f-URS) in which a soft renal pelvis ureter mirror (hereinafter, referred to as a flexible ureteroscope) is used. In a TUL, a calculus in a ureter or a renal pelvis and renal calyx may be directly reached extracorporeally, transvesically, or ureterily by using a hard mirror or a flexible ureteroscope so that the calculus may be directly broken or extracted. Therefore, advantages such that damage to a ureter, a kidney, or the like may be suppressed more and a high stone free rate may be realized in comparison with the ESWL or PNL are achieved. As an apparatus used in the TUL, an apparatus configured to remove a calculus generated in the ureter or the kidney or a plurality of broken calculus pieces generated after having broken the calculus by a laser to the outside of the body while retaining the same with a wire (basket forceps) is known. An example is disclosed in Japanese Application Publication No. 2001-512355.

The extraction of the stones by using the basket forceps is limited in gripping function of the basket forceps or the size of a ureteral lumen or a ureteral access sheath (guiding catheter), and hence the number of the calculi and the broken calculus pieces which may be removed in one operation is limited in a series of stone extracting operations from a step of gripping the broken calculus pieces to a step of carrying the gripped broken calculus pieces to the outside of the body with the basket forceps. Therefore, in order to remove the calculus, it is necessary to perform an insertion and a retraction of the basket forceps many times between the outside of the body and the position where the calculus exists. Accordingly, a user (operator) bears a heavy burden. In addition, various disadvantages for a patient occur such that a risk of, for example, developing an infection of a urinary tract or the like after the operation, and a burden to a ureter due to ischemia or the like generated due to a lengthening of an operation time for performing the insertion and the retraction of the basket forceps, and a risk of relapse increases because the calculi and the broken calculus pieces cannot be removed within a limited time of operation set for suppressing the infection after the operation.

By gripping a plurality of calculi, end surfaces of the calculi and the broken calculus pieces expose from a gap between metallic wires which constitute the basket forceps. Therefore, if an attempt is made to remove the plurality of calculi and the broken calculus pieces to the outside of the body at once, inner walls or the like of the kidney and the ureter may become damaged, or an end surface of an opening of a ureteral access sheath on a distal side and exposed portions of the calculi and the broken calculus pieces fit and hence cannot be pulled out to the outside of the body.

SUMMARY

The inventive calculus removing device is configured to remove a plurality of calculi and calculus broken pieces reliably to the outside of the body.

A calculus removing device including: a retaining portion configured to retain calculus; a collecting unit including: a storage portion configured to store the calculus therein; an opening communicating with the storage portion and through which the calculus is introduced into the storage portion; and an introducing portion configured to permit introduction of the retaining portion into the storage portion; a shaft portion provided with a lumen configured to receive the retaining portion to permit the retaining portion to be introduced into the storage portion via the introducing portion; and a hand-operated unit that includes an operating member that is operable to control an introduction of the retaining portion into the storage portion.

The collecting unit is provided with a through hole configured to communicate the lumen of the shaft portion with the storage portion.

The calculus removing device may be configured to include a plurality of the introducing portions formed in the collecting unit.

The plurality of introducing portions are spaced apart from each other on the storage portion in an axial direction from the opening toward a proximal end of the storage portion.

The introducing portion is formed at least in the vicinity of the opening.

The collecting unit includes a first storage portion configured to store the calculus, and a second storage portion configured to store the first storage portion so as to be mountable and demountable and coupled to the shaft portion.

The retaining portion introduced into the storage portion may be a linear member which may be pushed into voids defined by the calculi by operation of the operating member.

The retaining portion to be introduced into the storage portion may be a gel (gel-like) material capable of flowing into the voids defined by the calculi by operation of the operating member.

According to the calculus removing device disclosed here, since the calculi and the broken calculus pieces to be stored in the storage portion of the collecting unit may be retained in the retaining portion, the calculi and the broken calculus pieces may be retained reliably in the storage portion and removed to the outside of the body irrespective of the number or the size. Since the calculi and the broken calculus pieces are retained in the storage portion, the calculi and the broken calculus pieces may be removed safely and reliably to the outside of the body without causing the exposed end surfaces of the calculi and the broken calculus pieces to damage on a living tissue such as an inner wall or the like of the kidney or the ureter or to be caught when being pulled into the ureteral access sheath.

Because the collecting unit is capable of introducing the retaining portion into the storage portion along the through hole owing to the through hole (introducing portion) formed so as to communicate the lumen of the introduction tube with the storage portion, so that the calculi and the broken calculus pieces may be retained reliably in the storage portion.

By virtue of the plurality of introducing portions formed on the collecting unit, the retaining portion may be introduced into the storage portion from a plurality of positions, and so the calculus may be retained efficiently by using a plurality of the retaining portions. Even in the case where a plurality of the calculi and the broken calculus pieces including those of small sizes are densely positioned into the storage portion of the collecting unit, and hence the voids among the calculi and the broken calculus pieces and the storage portion are too small to allow the retaining portion to be introduced into the storage portion easily, the plurality of retaining portions may be used to retain the calculus and broken calculus pieces efficiently.

Positioning the plurality of introducing portions in axially spaced apart relation to each other from the opening toward the proximal side of the storage portion, allows the calculi and the broken calculus pieces collected from the opening toward the proximal side of the storage portion to be retained from a plurality of positions along an axial direction of the collecting unit, so that the calculi may be sufficiently retained by using the respective retaining portions.

Because the introducing portion is formed at least in the vicinity of the opening, the opening may be blocked rather easily by using the retaining portion, so that the calculi stored in the storage portion are prevented from dropping from the opening into the renal pelvis and renal calyx, the ureter, or the like and the calculi and the broken calculus pieces may be retained reliably in the storage portion.

By virtue of the collecting unit including the first storage portion configured to store the calculi and the broken calculus pieces and the second storage portion configured to store the first storage portion in a mountable and demountable manner, the first storage portion filled with the calculi and the broken calculus pieces may be demounted (separated or removed) from the second storage portion and a new first storage portion may be mounted in the second storage portion. Therefore, in the case where a pathological examination is performed with respect to the calculi and the broken calculus pieces and the calculi and the broken calculus pieces are discarded, the handling may be performed simply.

As described above, the retaining portion introduced into the storage portion may be a linear member which may be pushed into the void defined by the calculi and the broken calculus pieces by the operation of the operating member, and so the calculi and the broken calculus pieces may be firmly retained by using the linear member.

In the case of the retaining portion to be introduced into the storage portion being gel material capable of flowing into the void defined by the calculi and the broken calculus pieces by the operation of the operating member, the calculi and the broken calculus pieces may be firmly retained by using the gel-like material.

According to another aspect, a calculus removing device includes: a calculus collection housing, a shaft portion connected to the calculus collection housing, and a hand-operated unit connected to the shaft portion. The calculus collection housing is configured to be introduced into a living body and possesses an interior configured to receive and store calculus collected from the living body. The calculus collection housing including an opening which opens into the interior of the calculus collection housing and through which the calculus in the living body is introduced into the interior of the calculus collection housing. The hand-operated unit is configured so that at least a part of the retaining portion is located in the hand-operated unit. A lumen extends through the shaft portion and communicates with both the interior of the calculus collection housing and the hand-operated unit. The hand-operated unit comprises an operating member that is operable to move the retaining portion along the lumen and introduce the retaining portion into the interior of the calculus collection housing after the calculus is collected in the interior of the calculus collection housing to retain the calculus in the interior of the calculus collection housing.

According to another aspect, a method comprises: introducing a calculus collection housing into a living body, wherein the calculus collection housing possesses an interior and includes an opening which opens into the interior of the calculus collection housing; moving the calculus collection housing in the living body to position the opening of the calculus collection housing adjacent calculus in the living body; collecting the calculus in the interior of the calculus collection housing; and introducing a retaining portion into the interior of the calculus collection housing while the calculus is collected in the interior of the calculus collection housing to retain the calculus in the interior of the calculus collection housing and prevent the calculus collected in the interior of the calculus collection housing from moving out of the calculus collection housing.

DETAILED DESCRIPTION

Embodiments of the calculus removing device representing examples of the inventive calculus removing device disclosed here will be described with reference to the drawings. Dimensional ratios of the drawings may be exaggerated for the sake of easiness of description and may be different from actual ratios. For example, in a calculus removing device 10 illustrated in FIGS. 1A and 1B or the like, the sizes of a wire 11 and a cylinder 12 are significantly exaggerated in illustration in comparison with a hand-operated unit 14. The size of the calculus removing device 10 may be imagined by referring to that illustrated in FIG. 3. The side of a user (operator) where the hand-operated unit 14 exists corresponds to a proximal side or proximal end, and the side of a living body where the calculus removing device 10 or the like is introduced corresponds to a distal side or distal end.

First Embodiment

The calculus removing device 10 of a first embodiment will be described.

A configuration of the calculus removing device 10 will be described with reference to FIGS. 1A and 1B.

Figure 1A:
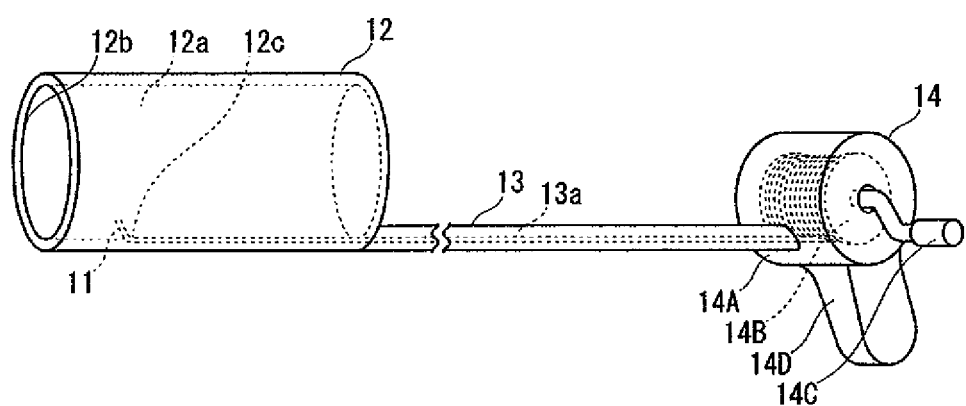
FIG. 1A is a perspective view of a calculus removing device of a first embodiment illustrating a state before introducing a retaining portion into a collecting unit.
Figure 1B:
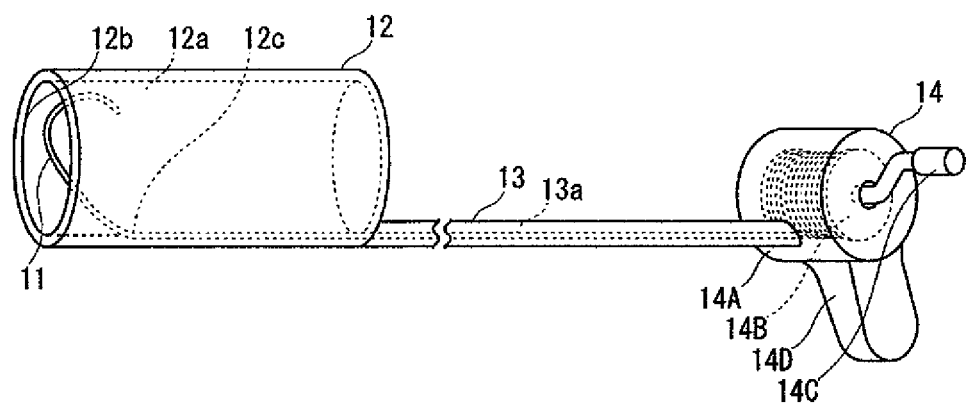
FIG. 1B is a perspective view of the calculus removing device of the first embodiment illustrating a state after the retaining portion has been introduced from an introducing portion of the collecting unit to a storage portion.

FIGS. 1A and 1B are perspective views of the calculus removing device 10 of the first embodiment. FIG. 1A illustrates the calculus removing device 10 in a state before introducing the wire 11 into the cylinder 12. FIG. 1B illustrates the calculus removing device 10 in a state after the wire 11 has been introduced from an introducing portion 12c of the cylinder 12 into a storage portion 12a.

The calculus removing device 10 collects a calculus K and broken calculus pieces generated in a ureter 230 or the like and removes the calculus K and the broken calculus pieces to the outside of a body and/or into a bladder in a state of being retained by twining with the wire 11. The calculus K and the broken calculus pieces exist in a urinary tract. The broken calculus pieces include the calculus K existing in the urinary tract, in a form of being broken up by, for example, a laser breakup apparatus to relatively small pieces.

In the following description, the calculi K include the broken calculus pieces.

The calculus removing device 10 includes the wire 11 (which corresponds to a retaining member), the cylinder 12 (which corresponds to a collecting unit), an introduction tube 13 (which corresponds to a shaft portion), and the hand-operated unit 14.

Figure 4A:
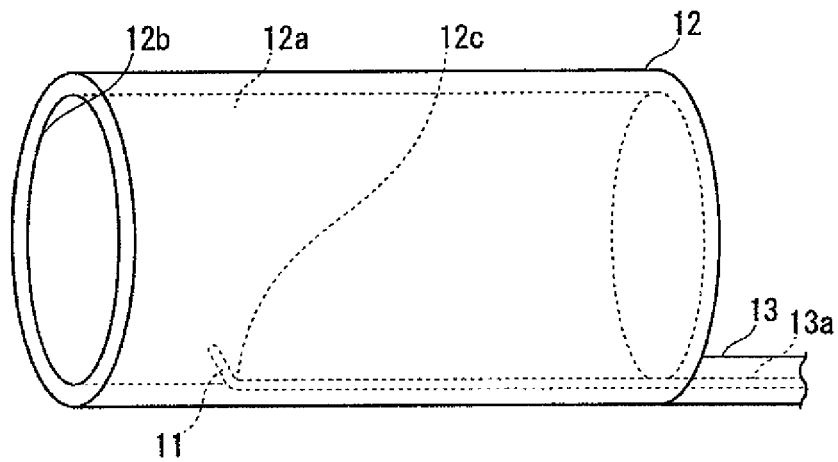
FIG. 4A is a schematic drawing of a state in which calculi and broken calculus pieces are collected in the collecting unit of the calculus removing device illustrating the storage portion of the collecting unit.
Figure 4B:
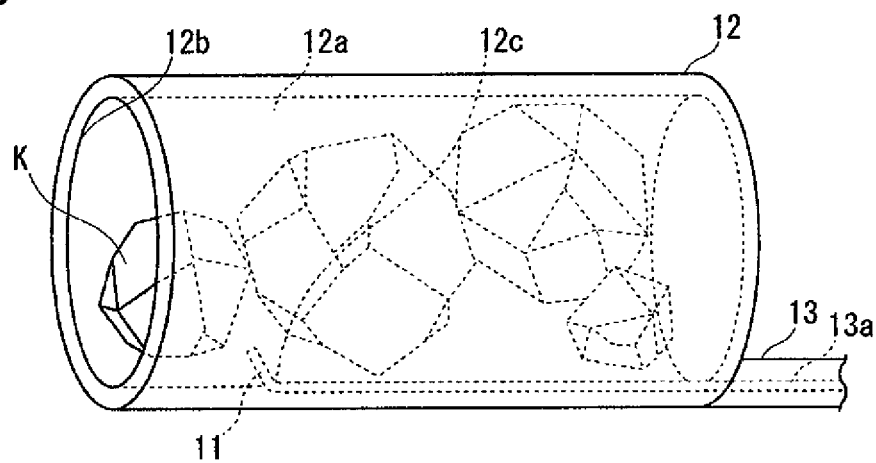
FIG. 4B is a schematic drawing of a state in which the calculi and the broken calculus pieces are collected in the collecting unit of the calculus removing device illustrating a state in which a plurality of the calculi and the broken calculus pieces are stored into the storage portion of the collecting unit.
Figure 4C:
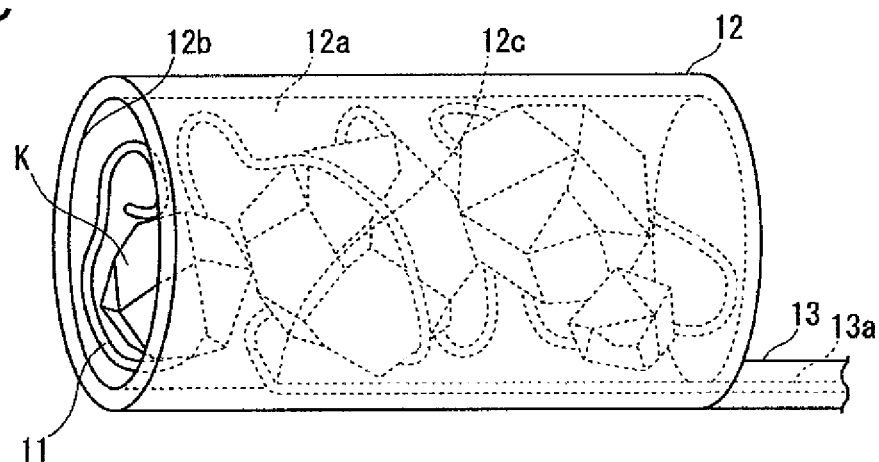
FIG. 4C is a schematic drawing of a state in which the calculi and the broken calculus pieces are collected in the collecting unit of the calculus removing device illustrating a state in which a plurality of the calculi and the broken calculus pieces are retained by being twined by the retaining portion introduced into the storage portion.

The wire 11 retains the calculi K collected in the storage portion 12a of the cylinder 12 (i.e., calculi K collected in the interior of the cylinder 12.) The wire 11 is fed out from the hand-operated unit 14, is inserted into or positioned in a lumen 13a of the introduction tube 13, and is introduced into the interior of the storage portion 12a via the introducing portion 12c of the cylinder 12. The wire 11 is configured as a linear member which may be pushed into voids among a plurality of the calculi K stored in the storage portion 12a by an operation of an operating member 14C. As illustrated in FIG. 4C, the wire 11 introduced into the storage portion meanders in the storage portion such that the wire 11 exhibits multiple turns and curves. The wire 11 is introduced into the voids among the calculi K, and retains the calculi K firmly together. The wire 11 is, for example, a metallic coil covered with a hydrophilic coat. The wire 11 may be a hydrocoil which is wound into a helical shape while swelling. The wire 11 is not limited to a metal wire, and may be formed of a yarn formed of bundled fibers, for example.

The cylinder 12 is a calculus collection housing that collects the calculi K. The cylinder 12 is provided with the storage portion 12a, an opening 12b at the distal end of the cylinder 12, and the introducing portion 12c. The storage portion 12a stores the calculi K. The storage portion 12a is formed into a cylindrical shape, is provided with the opening 12b at one end storage portion 12a, and a blocked proximal side, which corresponds to the other end. The storage portion 12a is formed of a material having flexibility, and may be deformed so as to match the shape of the ureter 230 or the like. The storage portion 12a is formed of a material which is transparent in a visible light region, so that a state of storage of the calculi K is visible from the outside. The opening 12b opens in communication with the storage portion 12a. The calculi K are stored in the storage portion 12a via the opening 12b. The introducing portion 12c is formed of a through hole which allows an introduction of the wire 11 into the storage portion 12a. The introducing portion 12c communicates the lumen 13a of the introduction tube 13 with the storage portion 12a. The introducing portion 12c opens toward an inner peripheral surface of the storage portion 12a. The cylinder 12 may have a configuration in which the position of the cylinder 12 in the living body may be confirmed by being or viewed fluoroscopically from the outside in a state of being filled with a radiographic contrast agent.

The introduction tube 13 allows the introduction of the wire 11 carried out from the hand-operated unit 14 and carried into the storage portion 12a. The introduction tube 13 possesses an elongated cylindrical shape, and is provided with the lumen 13a which allows the introduction of the wire 11 into the storage portion 12a via the introducing portion 12c. The introduction tube 13 is joined at one end to the cylinder 12, and coupled so as to be demountable and mountable at the other end which corresponds to the proximal side or proximal end to the hand-operated unit 14. The introduction tube 13 is formed of a material having flexibility, and may be deformed so as to match the shape of the ureter 230 or the like and the movement of a flexible ureteroscope 100.

The hand-operated unit 14 is configured to perform operations such as the introduction of the wire 11 into the storage portion 12a of the cylinder 12 by the user (operator) and an adjustment of the position of the cylinder 12 which is introduced into the ureter 230. The hand-operated unit 14 is provided with a retaining member 14A, a winding member 14B, the operating member 14C, and a gripping member 14D. The retaining member 14A corresponds to a main body of the hand-operated unit 14. The retaining member 14A is cylindrically shaped, and is coupled to the proximal side or proximal end of the introduction tube 13 so as to be demountably mountable by fitting or press fitting. The gripping member 14D is connected to a lower portion of the retaining member 14A. The retaining member 14A stores the winding member 14B. The winding member 14B possesses a column shape, and is wound by the wire 11.

The operating member 14C is configured to operate the introduction of the wire 11 into the storage portion 12a. The operating member 14C is formed, for example, of a handle and is coupled to the winding member 14B. The operating member 14C may be configured to be coupled to both sides of the winding member 14B so that the user (operator) can operate with his/her right hand and left hand. As illustrated in FIG. 1B, if the user (operator) rotates the operating member 14C, the winding member 14B rotates correspondingly, so that the wire 11 is introduced into the storage portion 12a of the cylinder 12. If the user (operator) rotates the operating member 14C in the opposite direction from the case where the wire 11 is introduced into the storage portion 12a of the cylinder 12, the wire 11 introduced into the storage portion 12a of the cylinder 12 is introduced into the introduction tube 13 and the hand-operated unit 14 via the introducing portion 12c. The gripping member 14D is a member gripped by the user (operator). The gripping member 14D is connected to the lower portion of the retaining member 14A.

A manner of using the calculus removing device 10 will be described with reference to FIG. 2 to FIG. 4C.

Figure 2:
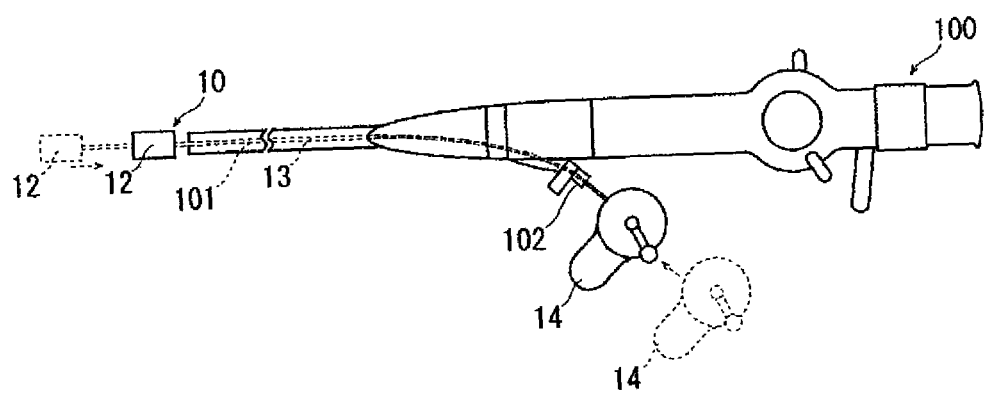
FIG. 2 is a schematic drawing illustrating a state in which the calculus removing device is mounted on a flexible ureteroscope.
Figure 3:
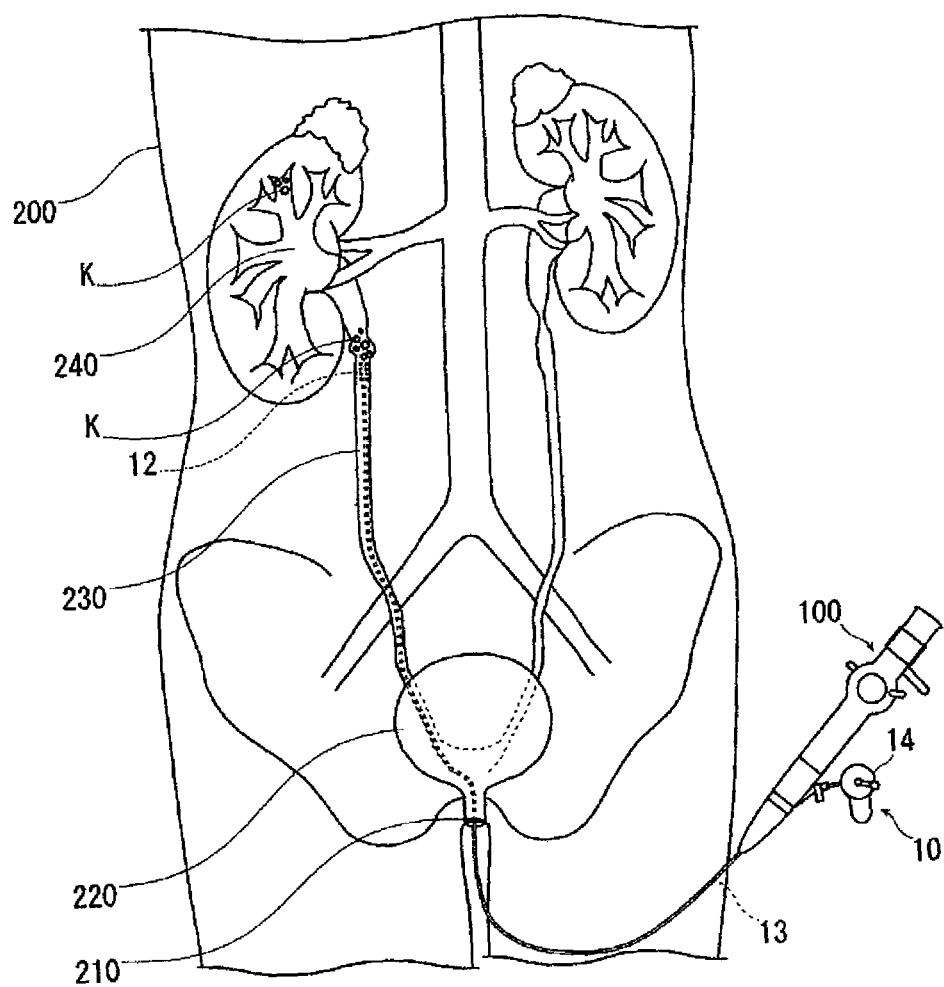
FIG. 3 is a schematic drawing illustrating a state in which the flexible ureteroscope on which the calculus removing device is mounted is introduced into a ureter of a patient.

FIG. 2 is a schematic drawing illustrating a state in which the calculus removing device 10 is mounted on the flexible ureteroscope 100. FIG. 3 is a schematic drawing illustrating a state in which the flexible ureteroscope 100 on which the calculus removing device 10 is mounted is introduced into the ureter 230 of a patient 200. FIGS. 4A to 4C are schematic drawings illustrating a state in which the calculi K are collected in the cylinder 12 of the calculus removing device 10. FIG. 4A is a drawing illustrating the storage portion 12a of the cylinder 12. FIG. 4B is a drawing illustrating a state in which the plurality of calculi K is stored in the storage portion 12a of the cylinder 12. FIG. 4C is a drawing illustrating a state in which the plurality of calculi K are twined and retained by the wire 11 introduced into the storage portion 12a.

A cystoscope, which is generally used in the urinary system is used for the patient 200 illustrated in FIG. 3, and a guide wire widely known in a medical field is introduced into the ureter 230 or a renal pelvis and renal calyx 240 via a urethra 210 and a bladder 220. Subsequently, a rigid ureteroscope is inserted to monitor an inner wall of the ureter 230 and the calculi K in the ureter 230. At this time, the calculi K may be removed by using a basket forceps together with the rigid ureteroscope. The calculi K which are relatively large and are difficult to remove may be broken into relatively small pieces using a breaking device such as a Ho: YAG laser or the like together with the rigid ureteroscope. The created broken calculus pieces may then be removed using the basket forceps. Subsequently, the rigid ureteroscope is removed from the living body.

Subsequently, a ureteral access sheath is introduced into the ureter 230 or the renal pelvis and renal calyx 240 via the urethra 210 and the bladder 220 via the guide wire.

The flexible ureteroscope 100 is inserted via the ureteral access sheath to monitor the calculi K. At this time, the guide wire may be removed. In the case where the calculi K have a relatively large size which makes the calculi K difficult to pass through the ureteral access sheath, the calculi K are broken into a relatively small size using the breaking device such as Ho: YAG laser or the like together with the flexible ureteroscope 100.

Subsequently, the calculus removing device 10 and the flexible ureteroscope 100 are assembled. Specifically, as illustrated in FIG. 2, from a state in which the introduction tube 13 and the hand-operated unit 14 of the calculus removing device 10 are separated, the introduction tube 13 is introduced into a working channel 101 of the flexible ureteroscope) 00 from a distal side or distal end of the flexible ureteroscope 100, the proximal end of the introduction tube 13 is taken out from a port 102, and the proximal end of the introduction tube 13 is fitted in and mounted on the hand-operated unit 14.

As illustrated in FIG. 3, the calculi K are collected in the cylinder 12 by using the calculus removing device 10 after the flexible ureteroscope 100 provided with the calculus removing device 10 mounted thereon has reached a portion in the ureter 230 where the calculi K exist via the urethra 210 and the bladder 220 of the patient 200. Specifically, the storage portion 12a of the cylinder 12 illustrated in FIG. 4A is pressed against the calculi K in the ureter 230 illustrated in FIG. 3 from the side of the hand-operated unit 14. In order to store the calculi K in the storage portion 12a efficiently (i.e., in order to collect calculus in or move calculus into the storage portion 12a), the storage portion 12a may be pushed and pulled from the hand-operated unit 14 side a plurality of times. As illustrated in FIG. 4B, the calculi K are stored in the storage portion 12a via the opening 12b of the cylinder 12. As illustrated in FIG. 4C, the wire 11 is introduced into the storage portion 12a of the cylinder 12, and the plurality of calculi K are retained by being twined with the wire 11. That is, the wire 11 introduced into the storage portion 12a of the cylinder 12 winds or spirals around the calculi K in a way that holds or retains the calculi K. The wire 11 is introduced into the voids among the calculi K, and retains the calculi K firmly together.

Subsequently, the calculus removing device 10 which has collected the calculi K in the cylinder 12 is carried or moved to the outside of the body. On the outside of the body, the wire 11 introduced into the storage portion 12a of the cylinder 12 may be introduced into the introduction tube 13 (i.e., the wire 11 may be withdrawn from the cylinder 12 and drawn back into the introduction tube 13) and the hand-operated unit 14 via the introducing portion 12c. Then, voids exist again among the calculi K, and the calculi K are removed rather easily from the storage portion 12a.

Again, after the calculus removing device 10 has reached a portion where the calculi K exist, the operations involving drawing the calculi K into the storage portion 12a and removing the calculi K from the living body to outside of the body are repeated. A portion where the calculi K are removed from the storage portion 12a may be within the bladder. In addition, for the purpose of changing the position of the calculi K (repositioning), the calculi K may be taken into the storage portion 12a in a renal calyx within the renal pelvis and renal calyx and be released in another renal calyx.

The calculus removing device 10 may be used together with the rigid ureteroscope. In other words, in the operation including the monitoring with the rigid ureteroscope, breakup of the stones, and extraction of the stone to be performed prior to the operation of extraction of the stone with the flexible ureteroscope 100, the calculus removing device 10 may be used instead of the basket forceps.

Subsequently, the guide wire is introduced into the ureter 230 or the renal pelvis and renal calyx 240 via the urethra 210 and the bladder 220. In addition, an indwelling ureter stent for the upper ureter is indwelled so as to cover the guide wire, and then the guide wire is pulled out. The ureter stent is used for preventing a transient blockage of the ureter or the like after the operation. The ureter stent is removed after a predetermined number of days have elapsed.

The technique described with reference to FIG. 2 to FIG. 4C is mainly as follows. The technique involves a method of collecting the calculi K by introducing a device into the living body of the patient 200 and removing the device to the outside of the body. More specifically, the method includes preparing the calculus removing device 10 configured to retain the calculi K stored in the storage portion 12a of the cylinder 12 with the wire 11, introducing the calculus removing device 10 mounted on the rigid ureteroscope or the flexible ureteroscope 100 into the living body, and retaining the calculi K stored in the storage portion 12a with the wire 11 and removing the calculi K to the outside of the body via the opening 12b of the cylinder 12.

As described above, according to the calculus removing device 10 of the first embodiment, the calculi K stored in the storage portion 12a of the cylinder 12 may be retained with the wire 11, so that the calculi K are reliably retained in the storage portion 12a and removed to the outside of the body.

In addition, since the calculus removing device 10 is configured to store the plurality of calculi K at once in the storage portion 12a, a removal efficiency of the calculi K may be significantly improved. In other words, by using the calculus removing device 10, the time required for removing the plurality of calculi K may be significantly reduced, and a larger number of the calculi K may be removed within a certain period of time. In the TUL, even though the upper limit of the time for the surgical operation is limited for preventing development or the like of an infection of the urinary tract after the surgical operation, a larger number of the calculi K may be removed to the outside of the body using the calculus removing device 10, so that the stone free rate may be improved.

In addition, since the calculus removing device 10 is capable of storing a plurality of calculi K having different sizes in the storage portion 12a, the calculi K having relatively small sizes and the large calculi K can be removed at once (i.e., at the same time).

In addition, since the calculus removing device 10 is capable of storing the calculi K into the storage portion 12a, the calculi K removed from the ureter 230 or the like may be removed to the outside of the body without coming into contact with and causing rupture of an inner wall of the ureter 230 or the bladder 220.

In addition, since the calculus removing device 10 is capable of storing the calculi K into the storage portion 12a, the calculi K removed from the ureter 230 or the like may be removed to the outside of the body without engaging the opening of the ureteral access sheath and making the ureteral access sheath difficult to be pulled out.

Since the cylinder 12 is capable of introducing the wire 11 into the storage portion 12a along the through hole owing to the through hole (introducing portion 12c) formed so as to communicate the lumen 13a of the introduction tube 13 with the storage portion 12a, the calculi K may be reliably retained in the storage portion 12a. In addition, since the cylinder 12 may be introduced into the storage portion 12a without causing the wire 11 to interfere with the ureter 230, the cylinder 12 or the like, the calculi K may be retained reliably in the storage portion 12a without causing damage of the ureter 230, the bladder 220 and the like with the wire 11.

Since the retaining portion to be introduced into the storage portion 12a includes the wire 11 which may be pushed into the voids defined by the calculi K by operation of the operating member 14C, the calculi K may be retained firmly by using the wire 11.

First Modification of First Embodiment

A calculus removing device of a first modification of the first embodiment, which generally involves a modified version of the cylinder 12, will be described. Cylinders 12S, 12T, and 12U of the calculus removing device are modified versions of the cylinder 12 of the calculus removing device 10 according to the first embodiment described above. In the first modification of the first embodiment, features which are the same as in the first embodiment are identified by common reference numerals, and a detailed description of such features is not repeated.

A configuration of cylinders of the calculus removing device will be described with reference to FIGS. 5A to 5C.

Figure 5A:
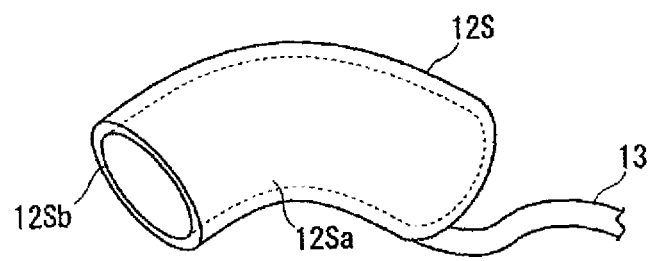
FIG. 5A is a perspective view of the collecting unit having various modes of the calculus removing device according to a first modification of the first embodiment illustrating the collecting unit formed to curve along an axial direction.
Figure 5B:
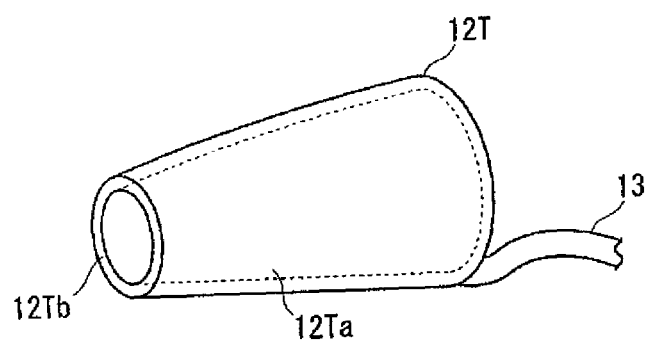
FIG. 5B is a perspective view of the collecting unit having various modes of the calculus removing device according to the first modification of the first embodiment illustrating the collecting unit formed so as to increase in an inner diameter and an outline from the opening to a proximal side.
Figure 5C:
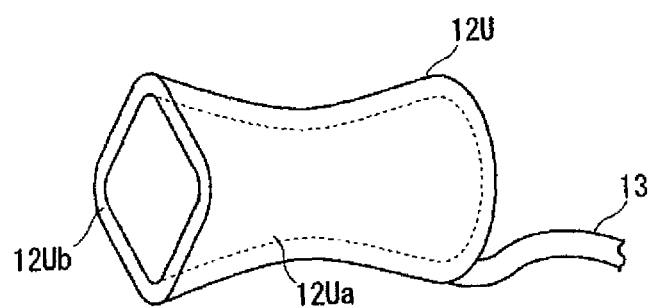
FIG. 5C is a perspective view of the collecting unit having various modes of the calculus removing device according to the first modification of the first embodiment illustrating the collecting unit formed so as to have the rectangular opening and having a diameter partly reduced in diameter toward the proximal side.

FIGS. 5A to 5C are perspective views of various forms of the cylinders of the calculus removing device of the first modification of the first embodiment. FIG. 5A is a drawing illustrating the cylinder 12S formed so as to curve along an axial direction. FIG. 5B is a drawing illustrating the cylinder 12T formed so as to be increased in an inner diameter and an outline toward the proximal end from an opening 12Tb. FIG. 5C is a drawing illustrating the cylinder 12U having a rectangular opening 12Ub and a diameter reduced partly toward the proximal end.

In the calculus removing device illustrated in FIG. 5A, the cylinder 12S is different from the cylinder 12 and is configured to be curved along the axial direction to achieve a shape matching the shapes of the renal pelvis and renal calyx 240 and the ureter 230 of a specific patient 200. In the same manner, in the calculus removing device illustrated in FIG. 5B, the cylinder 12T is different from the cylinder 12 and is configured to be increased in the inner diameter and the outline toward the proximal side from the opening 12Tb to achieve a shape matching the shapes of the renal pelvis and renal calyx 240 and the ureter 230 of the specific patient 200. In the same manner, in the calculus removing device illustrated in FIG. 5C, the cylinder 12U is different from the cylinder 12 and is configured to have the rectangular opening 12Ub and a diameter reduced partly toward the proximal side in order to achieve a shape matching the shapes of the renal pelvis and renal calyx 240 and the ureter 230 of the specific patient 200.

As described above, according to the calculus removing device of the first modification of the first embodiment, since the shape matching the shape in the living body is achieved by the cylinder 12S formed into a curved shape along the axial direction or axial extent of the cylinder 12S, for example, a configuration that is relatively easy to introduce into the ureter 230 and the renal pelvis and renal calyx 240 is achieved. The shape in the living body corresponds to a shape of an inner periphery of the ureter 230. In addition, the calculus removing device is capable of retaining the calculi K reliably in a storage portion 12Sa since the calculi K stored in the storage portion 12Sa and moved to the proximal side may be prevented from returning back to an opening 12Sb side easily by catching or restraining the same by the curved storage portion 12Sa.

Since the calculus removing device may achieve the shape matching the shape in the living body by the cylinder 12T formed so as to be increased in an inner diameter and an outer size or outer diameter from the opening 12Tb toward the proximal side, for example, a configuration easy to introduce into the ureter 230 and the renal pelvis and renal calyx 240 is achieved. In addition, the calculus removing device is capable of retaining the calculi K reliably in a storage portion 12Ta since the calculi K stored in the storage portion 12Ta and moved to the proximal side may be prevented from easily returning back to the opening 12Tb side by virtue of the relatively small diameter. In addition, since the opening 12Tb having a relatively small diameter may be introduced more easily into narrow portions or the like such as the ureter 230 or a portion in the renal calyx in the vicinity of the renal papilla, the calculi K generated in the ureter 230 or the like may be more easily collected.

Since the calculus removing device may achieve the shape matching the shape in the living body by the cylinder 12U having the opening 12Ub of a rectangular shape and having a diameter reduced partly (reduced along a part of the axial extent of the cylinder 12U toward the proximal side, for example, a configuration more easily introduced into the ureter 230 and the renal pelvis and renal calyx 240 is achieved. In addition, since the calculus removing device is capable of introducing the calculi K easily from the rectangular opening 12Ub having a long distance on a diagonal line and, at the same time, the calculi K moved to the proximal side of a storage portion 12Ua may be prevented from returning back to the opening 12Ub side easily by the storage portion 12Ua having a relatively small diameter, so that the calculi K may be retained reliably in the storage portion 12Ua.

Modification 2 of First Embodiment

A calculus removing device of a second modification of the first embodiment which generally involves a modification of the operating member 14C will be described. Operating members 14P, 14Q, and 14R of the calculus removing device correspond to the modification of the operating member 14C of the calculus removing device 10 of the first embodiment described above. In the second modification of the first embodiment described above, features which are the same as in the first embodiment are identified by common reference numerals, and a detailed description of such features is not repeated.

A configuration of the hand-operated unit of the calculus removing device will be described with reference to FIGS. 6A to 6C.

Figure 6A:
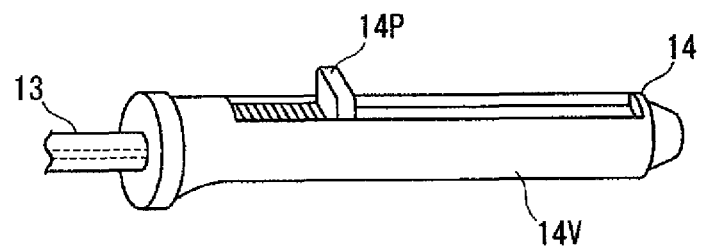
FIG. 6A is a perspective view of a hand-operated unit provided with an operating member having various modes of the calculus removing device according to a second modification of the first embodiment illustrating an operating member including a linear type sliding portion configured to be moved back and forth manually in the axial direction.
Figure 6B:
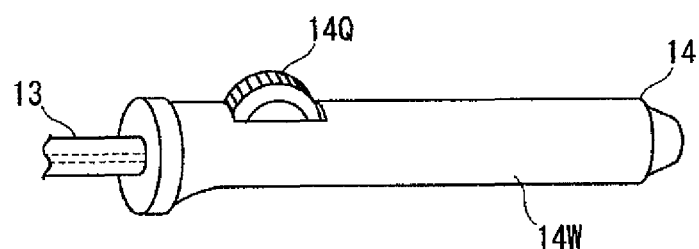
FIG. 6B is a perspective view of the hand-operated unit provided with the operating member having various modes of the calculus removing device according to the second modification of the first embodiment illustrating an operating member including the sliding portion configured to be manually rotated.
Figure 6C:
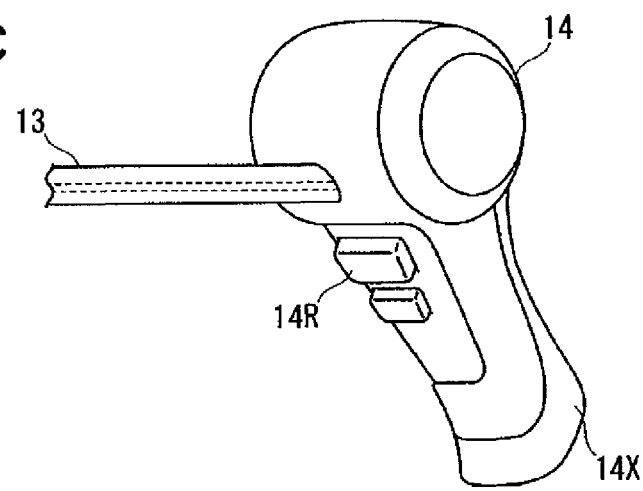
FIG. 6C is a perspective view of the hand-operated unit provided with the operating member having various modes of the calculus removing device according to the second modification of the first embodiment illustrating an operating member including a rotating portion configured to be controlled automatically.

FIGS. 6A to 6C are perspective views of the hand-operated unit having various forms of the operating members of the calculus removing device of the second modification of the first embodiment. FIG. 6A is a drawing illustrating the operating member 14P including a linear type sliding portion configured to be moved back and forth manually in the axial direction. FIG. 6B is a drawing illustrating the operating member 14Q including a rotary type sliding portion configured to be rotated manually. FIG. 6C is a drawing illustrating the operating member 14R including a rotating portion configured to be controlled automatically.

The calculus removing device illustrated in FIG. 6A is provided with the operating member 14P including the linear type sliding portion configured to be moved axially forward and rearward. The operating member 14P is possesses a rectangular shape and is connected to the proximal side of the wire 11. The operating member 14P is provided with a projecting portion so as to allow the thumb or the like to touch and operate the operating member 14P. When the operating member 14P is moved in the axial direction, the wire 11 connected to the operating member 14P moves correspondingly. A cylindrically-shaped gripping member 14V is provided to be gripped by the user, and the operating member 14P is mounted on the gripping member 14V. The gripping member 14V is coupled to the proximal end of the introduction tube 13.

The calculus removing device illustrated in FIG. 6B is provided with the operating member 14Q including the rotary type sliding portion configured to be rotated manually. The operating member 14Q possesses a column shape, and is in contact with and presses the wire 11. The operating member 14Q is provided with a plurality of grooves formed on an outer periphery surface of the operating member 14Q so as to achieve an easy-to-rotate configuration with the thumb or the like. When the operating member 14Q is rotated, the wire 11 pressed against the operating member 14Q moves correspondingly. The operating member 14Q is mounted on a cylindrically-shaped gripping member 14W. The gripping member 14W is coupled to the proximal end of the introduction tube 13.

The calculus removing device illustrated in FIG. 6C is provided with the operating member 14R including the sliding portion configured to be controlled automatically. The operating member 14R is provided with a motor, a circuit configured to control the motor, and a switch configured to issue a command to rotate the motor. The proximal end of the wire 11 is wound around a rotating shaft of the motor. When the motor is rotated/stopped by turning ON/OFF the switch, the wire 11 moves/stops correspondingly. The motor and the circuit are integrated in a gripping member 14X, and the switch is attached to the gripping member 14X. The gripping member 14X is coupled to the proximal side of the introduction tube 13.

As described above, the calculus removing device of the second modification of the first embodiment shown in FIG. 6A may be suitably applied in situations where the length of the wire 11 to be introduced into the storage portion 12a is relatively short because the length of the wire 11 to be introduced into the storage portion 12a may be recognized more easily by the operating member 14P including the linear type sliding portion which is configured to be manually rotated. In addition, an operation of the wire 11 to be introduced into the storage portion 12a is achieved by the hand gripping the hand-operated unit 14V, that is, by one hand.

The calculus removing device shown in FIG. 6B is suitably applied to the case where the length of the wire 11 to be introduced into the storage portion 12a is relatively long because the length of the wire 11 to be introduced into the storage portion 12a is not specifically limited by the operating member 14Q including the rotary type sliding portion which is configured to be manually rotated. In addition, the operation of the wire 11 to be introduced into the storage portion 12a is achieved by the hand gripping the hand operating unit 14W, that is, by one hand.

Since the calculus removing device shown in FIG. 6C is configured to operate the wire 11 to be introduced into the storage portion 12a automatically instead of manually by the operating member 14R including the sliding portion configured to be automatically controlled, the wire 11 may be introduced relatively easily into the storage portion 12a. In addition, an amount of feeding of the wire 11 to the storage portion 12a may be adjusted finely and may be adjusted constantly. In addition, the operation of the wire 11 to be introduced into the storage portion 12a may be achieved by the hand gripping the hand-operated unit 14X, that is, by one hand.

Second Embodiment

A calculus removing device 20 of a second embodiment will now be described. The calculus removing device 20 of this second embodiment is different from the calculus removing device 10 of the first embodiment described above in a configuration in which a plurality of the wires 11 are introduced into a storage portion 22a. In the second embodiment, features which are the same as in the first embodiment are identified by common reference numerals, and a detailed description of such features is not repeated.

The configuration of the calculus removing device 20 and a manner of using the calculus removing device 20 will be described with reference to FIGS. 7A and 7B.

Figure 7A:
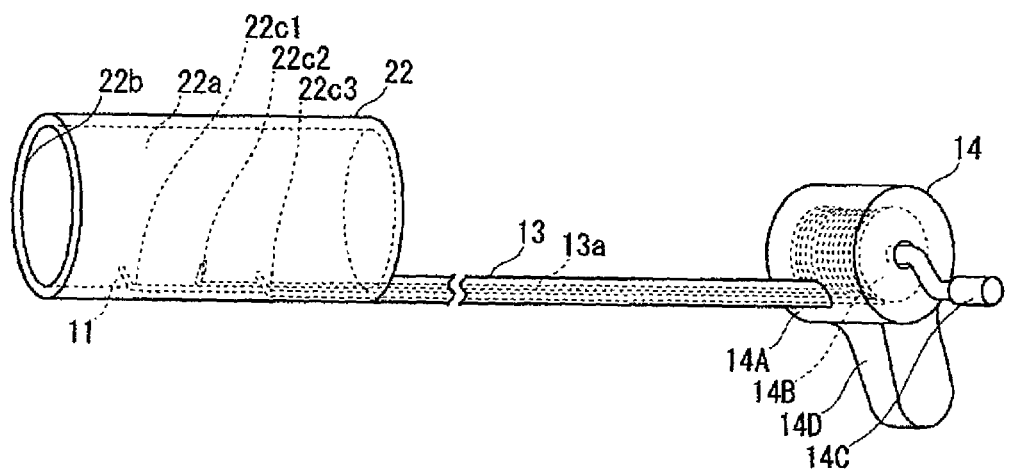
FIG. 7A is a perspective view of a calculus removing device of a second embodiment illustrating a state before introducing a plurality of the retaining portions into the collecting unit.
Figure 7B:
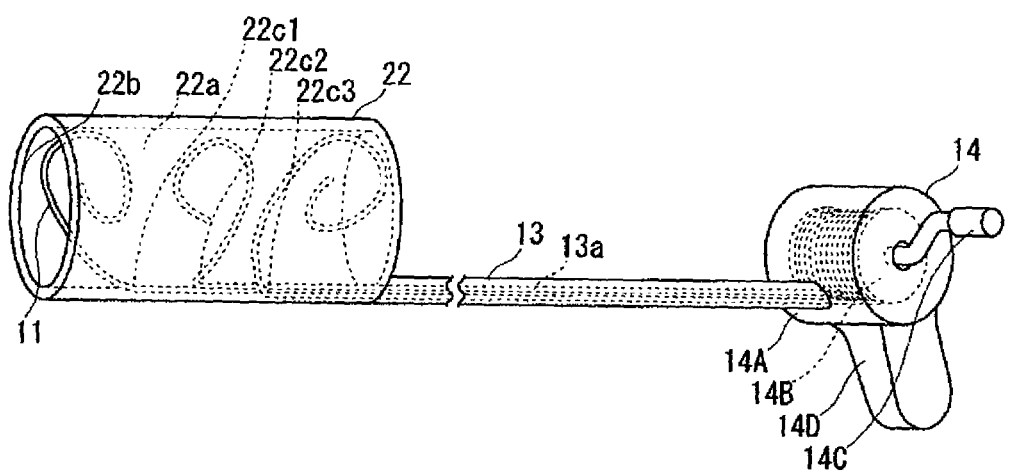
FIG. 7B is a perspective view of the calculus removing device of the second embodiment illustrating a state after the plurality of retaining portions are introduced from a plurality of introducing portions formed so as to be apart from each other along an axial direction of the collecting unit into the storage portion.

FIGS. 7A and 7B are perspective views illustrating the calculus removing device 20 of the second embodiment. FIG. 7A is a drawing illustrating a state before introducing the plurality of wires 11 into a cylinder 22. FIG. 7B is a drawing illustrating a state in which the plurality of wires 11 are introduced into the storage portion 22a from a plurality of introducing portions 22c1, 22c2, and 22c3 spaced apart from each other along the axial direction of the cylinder 22. In FIG. 7B, illustration of the calculi K is omitted.

The cylinder 22 has the same configuration as the cylinder 12 described above except for the number of the introducing portions. The cylinder 22 is provided with a plurality of the introducing portions 22c1, 22c2, and 22c3, and these introducing portions 22c1, 22c2, and 22c3 are spaced apart from each other along the axial direction from an opening 22b at the distal end toward the proximal end. The introducing portions 22c1, 22c2, and 22c3 are formed of through holes which are the same as the introducing portion 12c respectively, and each of the introducing portions 22c1, 22c2, and 22c3 introduces a respective one of the wires 11 into the storage portion 22a. The number of the introducing portions may be a plural and is not specifically limited.

The wire 11 introduced from the introducing portion 22c1 into the storage portion 22a retains the calculi K stored mainly in a vicinity of the opening 22b of the storage portion 22a by virtue of the wire 11 twining around such calculi K. The wire 11 introduced from the introducing portion 22c2 into the storage portion 22a retains the calculi K stored mainly in the vicinity of a center of the storage portion 22a by virtue of the wire 11 twining around such calculi K. The wire 11 introduced from the introducing portion 22c3 into the storage portion 22a retains the calculi K stored mainly on the proximal side of the storage portion 22a by virtue of the wire 11 twining around such calculi K. In the case where the introducing portions 22c1, 22c2, and 22c3 are introduced into (open into) the storage portion 22a at different angles with respect to the axial direction of the storage portion 22a, the plurality of wires 11 may be introduced from different angles, and hence the calculi K may be retained evenly all over.

The wires 11 for the introducing portions 22c1, 22c2, and 22c3 are wound around the winding member 14B of the hand-operated unit 14 respectively. If the operating member 14C of the hand-operated unit 14 is rotated, the winding member 14B rotates correspondingly, and the wires 11 for the introducing portions 22c1, 22c2, and 22c3 are respectively fed.

As described above, according to the calculus removing device 20 of the second embodiment, since the wires 11 may be introduced into the storage portion 12a from a plurality of the positions by a plurality of the introducing portions 22c1, 22c2, and 22c3 formed on the cylinder 22, the calculus K may be retained efficiently by using the plurality of wires 11.

Since the plurality of introducing portions 22c1, 22c2, and 22c3 are spaced apart from each other in the axial direction from the opening 22b toward the proximal end of the storage portion 22a, the calculi K collected from the opening 22b to the proximal end of the storage portion 22a may be retained at a plurality of positions along the axial direction of the cylinder 22, so that the calculi K may be sufficiently retained by using the respective wires 11.

Third Embodiment

A calculus removing device 30 of a third embodiment will be described. The calculus removing device 30 is different from the calculus removing device 10 or 20 of the first or second embodiment described above in terms of the manner by which the opening 12b of the cylinder 12 is blocked by the wire 11. In the third embodiment, features which are the same as in the first or second embodiments are identified by common reference numerals and a detailed description of such features is not repeated.

The configuration of the calculus removing device 30 and a manner of using the calculus removing device 30 will be described with reference to FIGS. 8A and 8B.

Figure 8A:
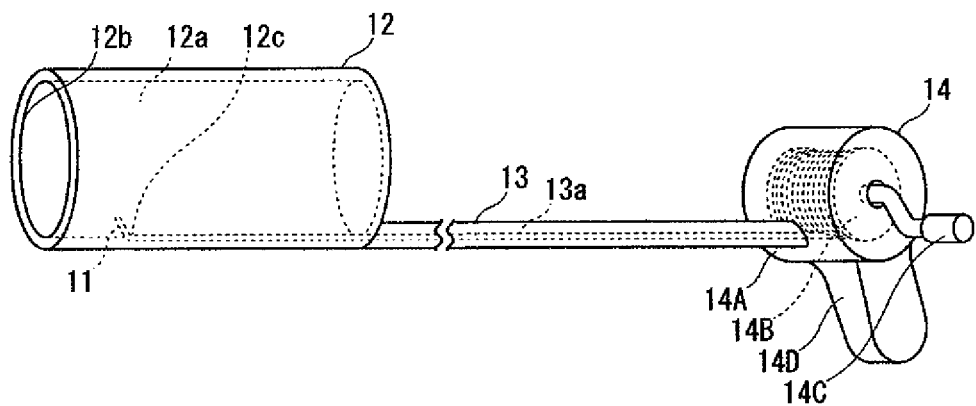
FIG. 8A is a perspective view of a calculus removing device of a third embodiment illustrating a state before introducing the retaining portion into the collecting unit.
Figure 8B:
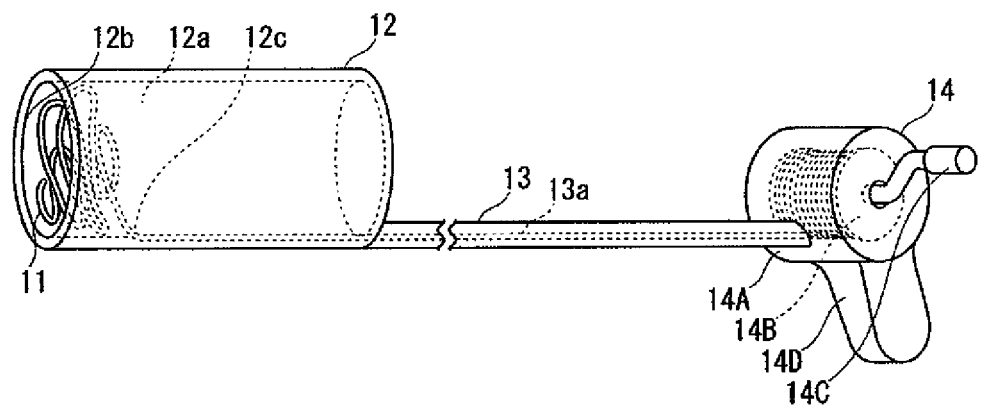
FIG. 8B is a perspective view of the calculus removing device of the third embodiment illustrating a state after the retaining portions have been introduced from the introducing portion of the collecting unit to the storage portion and the opening is blocked.

FIGS. 8A and 8B are perspective views illustrating the calculus removing device 30 of the third embodiment. FIG. 8A is a drawing illustrating a state before introducing the wire 11 into the cylinder 12. FIG. 8B is a drawing illustrating a state in which the wire 11 is introduced from the introducing portion 12c of the cylinder 12 into the storage portion 12a to block the opening 12b. In FIG. 8B, illustration of the calculi K is omitted.

When the operating member 14C of the hand-operated unit 14 is rotated, the opening 12b of the cylinder 12 is blocked by the wire 11 introduced from the introducing portion 12c into the storage portion 12a. In other words, the wire 11 introduced into the storage portion 12a is wound a plurality of times in the vicinity of the opening 12b to block the opening 12b.

Here, for example, the wire 11 is formed of a shape-memory alloy such as NiTi alloy so as to assume or take on a circular shape along a circumferential direction of the storage portion 12a, so that the wire 11 introduced from the introducing portion 12c into the storage portion 12a is wound along an outer peripheral edge of the opening 12b. In this configuration, the opening 12b can be selectively blocked by the wire 11. For example, with the introducing portion 12c formed of a groove extending along the circumferential direction of the storage portion 12a, the wire 11 introduced from the introducing portion 12c into the storage portion 12a is wound along the outer peripheral edge of the opening 12b.

In the calculus removing device 30, the wire 11 does not need to be introduced between the plurality of calculi K stored in the storage portion 12a, so that the storage efficiency of the calculi K is improved by storing the plurality of calculi K so as to be in tight contact with each other.

As described thus far, according to the calculus removing device 30 of the third embodiment, since the introducing portion 12c is formed at least in the vicinity of the opening 12b, the opening 12b can be blocked more easily by using the wire 11, so that the calculi K stored in the storage portion 12a are prevented from dropping from (falling out of) the opening 12b into the ureter 230 or the like, and the calculi K can be retained more reliably in the storage portion 12a.

Fourth Embodiment

A calculus removing device 40 of a fourth embodiment will be described. The calculus removing device 40 is different from the calculus removing devices 10, 20, and 30 of the first to third embodiments described above in that a gel-like material 41 (gel material) is used as a retaining portion to be introduced into the storage portion 12a for retaining the calculi K. In the fourth embodiment, features which are the same as in the first, second or third embodiment are identified by common reference numerals and a detailed description of such features is not repeated.

The configuration of the calculus removing device 40 and a manner of using the calculus removing device 40 will be described with reference to FIGS. 9A and 9B.

Figure 9A:
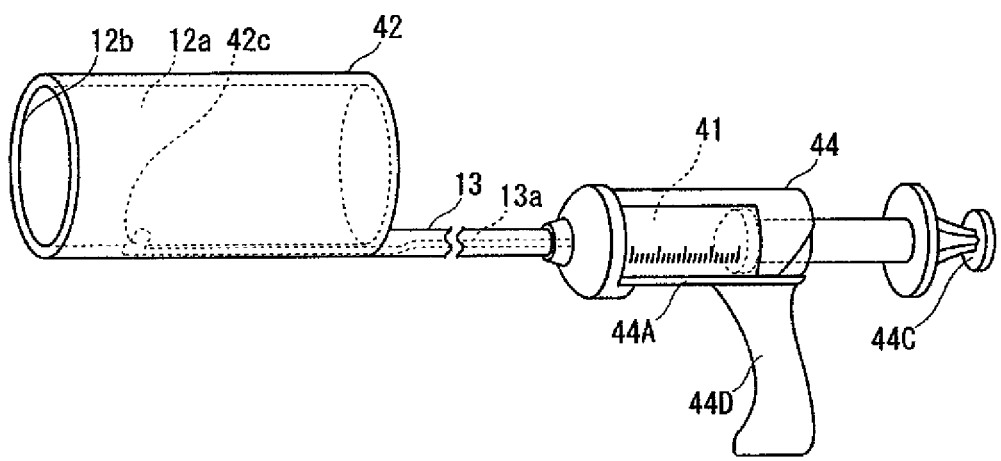
FIG. 9A is a perspective view of a calculus removing device of a fourth embodiment illustrating a state before introducing a gel-like material into the collecting unit.
Figure 9B:
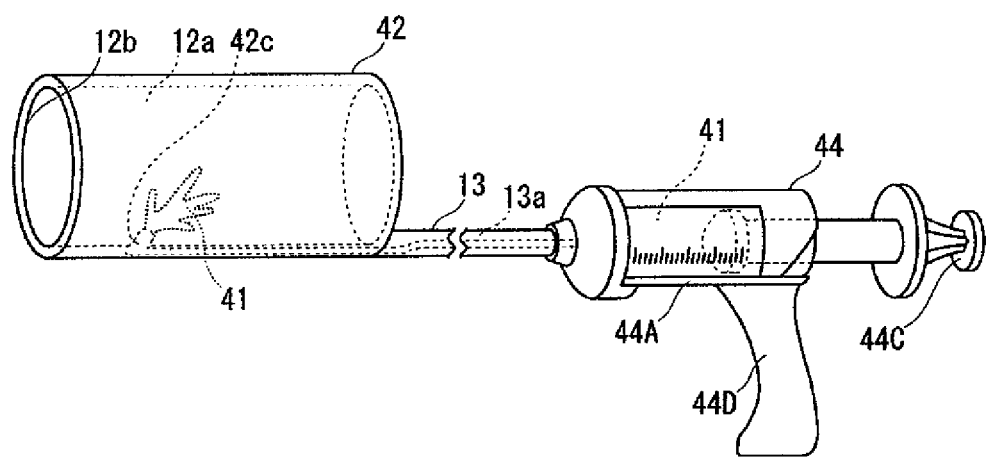
FIG. 9B is a perspective view of the calculus removing device of the fourth embodiment illustrating a state after the gel-like material has been introduced from an introducing portion of the collecting unit to the storage portion.

FIGS. 9A and 9B are perspective views illustrating the calculus removing device 40 of the fourth embodiment. FIG. 9A is a drawing illustrating a state before introducing the gel-like material 41 into a cylinder 42. FIG. 9B is a drawing illustrating a state in which the gel-like material 41 has been introduced from an introducing portion 42c of the cylinder 42 into the storage portion 12a. In FIG. 9B, illustration of the calculi K is omitted.

The cylinder 42 has the same configuration as that of the cylinder 12 described above except for the introducing portion 42c. The introducing portion 42c slightly projects inward of the storage portion 12a, and is inclined toward the proximal side or proximal end. The gel-like material 41 to be introduced into the cylinder 42 from the introducing portion 42c is introduced toward the proximal side or proximal end of the storage portion 12a so that the gel-like material is spaced from the opening 12b.

The gel-like material 41 is introduced into the storage portion 12a via the introducing portion 42c and fills the voids among the calculi K. An example of a gel-like material (gel material) that can be used is a reactive gelatinizing agent that cures gradually. The gel-like material 41 is preferably one having viscosity in which the gel material is in an injectable liquid state before gelatinization.

A hand-operated unit 44 is provided with an operating member 44C configured to be operated to introduce the gel-like material 41 into the storage portion 12a. The operating member 44C includes, for example, a syringe, and is filled with the gel-like material 41 in the interior of the syringe. A retaining member 44A stores part of the operating member 44C. The retaining member 44A is coupled to the proximal side of the introduction tube 13 and is connected to a gripping member 44D. When the operating member 44C is pressed by a thumb or the like, the gel-like material 41 is introduced into the storage portion 12a of the cylinder 42 via the lumen 13a of the introduction tube 13 and the introducing portion 42c from the interior of the syringe of the operating member 44C.

As described above, according to the calculus removing device 40 of the fourth embodiment, the retaining portion introduced into the storage portion 12a includes the gel-like material 41 which is able to flow into the voids defined by the calculi K by an operation of the operating member 44C, the calculi K may be firmly retained by the gel-like material 41.

Fifth Embodiment

A calculus removing device 50 of a fifth embodiment will be described. The calculus removing device 50 is different from the configurations of the calculus removing device 10, 20, 30, and 40 of the first to fourth embodiments described above in that an inner cylinder 52M constituting the first storage portion configured to store the calculi K is mountable on and demountable from an outer cylinder 52N constituting the second storage portion. In the fifth embodiment, features which are the same as in the first thru fourth embodiments are identified by common reference numerals and a detailed description of such features is not repeated.

The configuration of the calculus removing device 50 and a manner of using the calculus removing device 50 will be described with reference to FIGS. 10A and 10B.

Figure 10A:
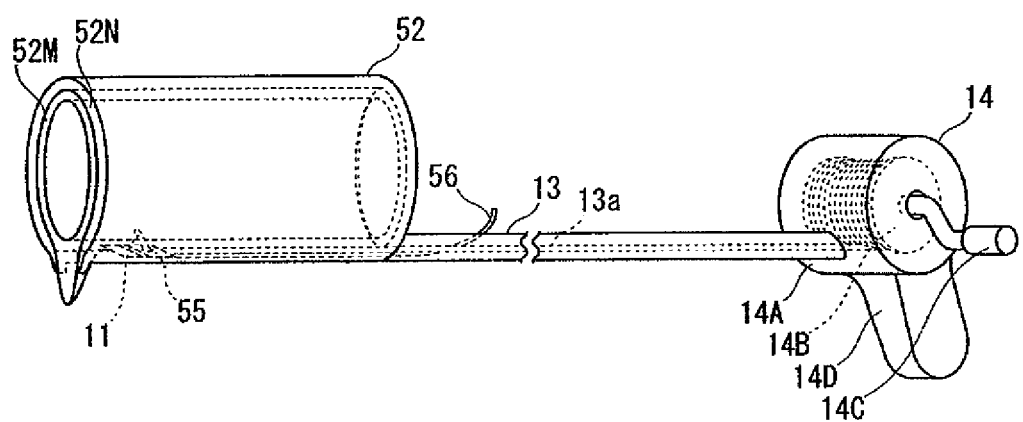
FIG. 10A is a perspective view of a calculus removing device of a fifth embodiment illustrating the collecting unit of a state in which a first storage portion is stored in a second storing portion.
Figure 10B:
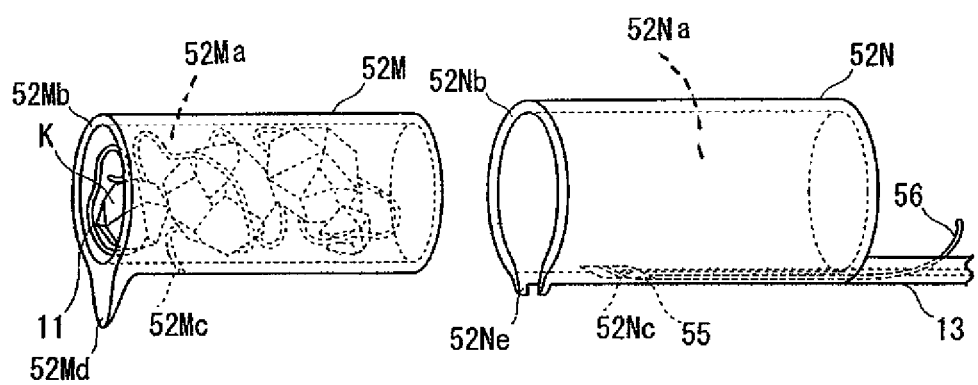
FIG. 10B is a perspective view of the calculus removing device of the fifth embodiment illustrating the collecting unit in a state in which the first storage portion which retains the plurality of calculi and the broken calculus pieces in a state of being twined is removed from the second storage portion.

FIGS. 10A and 10B are perspective views illustrating the calculus removing device 50 of the fifth embodiment. FIG. 10A is a drawing illustrating a cylinder 52 in a state in which the inner cylinder 52M is stored in the outer cylinder 52N. FIG. 10B is a drawing illustrating the cylinder 52 in a state in which the inner cylinder 52M in which the plurality of calculi K are twined and retained is removed from the outer cylinder 52N.

The cylinder 52 includes the inner cylinder 52M and the outer cylinder 52N. The inner cylinder 52M stores the calculi K. The inner cylinder 52M possesses a cylindrical shape and the proximal end of the inner cylinder 52M opposing the open distal end 52Mb is blocked. A storage portion 52Ma is provided with an introducing portion 52Mc configured to introduce the wire 11 opened therein The inner cylinder 52M is provided with a gripping portion 52Md configured to be gripped with fingertips to separate the inner cylinder from the outer cylinder 52N at the opening 52Mb. The gripping portion 52Md is a projecting part that slightly projects outward from an outer peripheral edge of the opening 52Mb of the inner cylinder 52M.

The outer cylinder 52N stores or houses the inner cylinder 52M so that the inner cylinder 52M is demountable and mountable with respect to the outer cylinder 52N, and is coupled with the introduction tube 13. The outer cylinder 52N possesses a cylindrical shape, and the proximal end of the outer cylinder 52N facing an opening 52Nb is blocked. An inner diameter of the outer cylinder 52N corresponds to an outer diameter of the inner cylinder 52M.

A storage portion 52Na of the outer cylinder 52N includes an introducing portion 52Nc configured to introduce the wire 11 opened therein. The outer cylinder 52N is provided with a supporting portion 52Ne which serves as a position identification or position identifier when separating from the inner cylinder 52M at the opening 52Nb. The supporting portion 52Ne is formed at the outer peripheral edge of the opening 52Mb so as to be depressed (i.e., the supporting portion 52Ne is a depression, recess or groove). The gripping portion 52Md of the inner cylinder 52M is inserted into or positioned in the supporting portion 52Ne of the outer cylinder 52N.

The wire 11 is cut by a cutter 55 before removing the inner cylinder 52M from the outer cylinder 52N. One end of a string 56 is connected to the cutter 55, and the other end of the string 56 is exposed to the outside via the lumen 13a of the introduction tube 13. If the other end of the string 56 is pulled, the cutter 55 moves and the wire 11 is cut. The cutter 55 may be a plate-shaped cutter provided in an interior of the outer cylinder 52N, or may be a curved plate-shaped cutter 55 provided in a gap between the inner cylinder 52M and the outer cylinder 52N. In an alternative configuration in which the string 56 is not provided, the cutter 55 may be fixed to the outer cylinder 52N, with the wire 11 in tight contact with the cutter 55 when removing the inner cylinder 52M from the outer cylinder 52N, so that the wire 11 is cut by the cutter 55 without operating the string 56 by removing the inner cylinder 52M from the outer cylinder 52N.

As described thus far, according to the calculus removing device 50 of the fifth embodiment, since the cylinder 52 includes the inner cylinder 52M configured to store the calculi K and the outer cylinder 52N configured to store the inner cylinder 52M in a mountable/demountable manner and coupled to the introduction tube 13, the inner cylinder 52M filled with the calculi K may be demounted or separated from the outer cylinder 52N and a new inner cylinder 52M may be mounted in the outer cylinder 52N. Therefore, in the case where a pathological examination is performed with respect to the calculi K and where the calculi K are discarded, the handling may be performed relatively simply. In addition, in the case where the plurality of calculi K cannot be collected in the cylinder 52 at once, removal of the calculi K may be continued by simply replacing the inner cylinder 52M.

Although the inventive calculus removing device disclosed here has been described through a plurality of embodiments, modifications and the like, the invention may be modified within the scope of the attached Claims.

For example, the calculus removing device is not limited to a form in which the calculi K may be removed by introducing the device into the ureter 230, but a form in which the calculi K may be removed by introducing the device into other portions in the living body. The interior of the living body corresponds, for example, to the renal pelvis and renal calyx 240.

As another example, a configuration of the cylinder 12 may be such that the introducing portion 12c configured to introduce the wire 11 into the storage portion 12a is not limited to the through hole which communicates from the lumen 13a of the introduction tube 13 to the storage portion 12a, and may be provided at part of the outer peripheral edge of the opening 12b. In this configuration, the introducing portion 12c may be embodied by very simple specifications.

A configuration in which each of the plurality of wires 11 is introduced from the single introducing portion 12c into the storage portion 12a in the cylinder 12 is also applicable. In this configuration, the calculi K can be retained further easily.

According to another example, a configuration of the cylinder 12 in which a pair of the introducing portions 12c are provided so as to face each other along concentric circles of the inner peripheral surface of the storage portion 12a, or a plurality of the introducing portions 12c may be provided at predetermined intervals along the concentric circles is also applicable. In this configuration, the calculi K stored in the storage portion 12a may be retained by the wire 11 so as to be pressed from a plurality of directions.

The retaining portion configured to retain the calculi K may be composed of the wire 11 and the gel-like material 41 in combination. In this configuration, the calculi K can be retained in the storage portion 12a further reliably.

The detailed description above describes embodiments of a calculus removing device and manner of use representing examples of the inventive calculus removing device and manner of use disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A calculus removing device comprising:
 a retaining portion configured to retain calculus;
 a collecting unit including:
  a storage portion configured to store the calculus in the storage portion, the storage portion including one end and an axially oppositely located other end;
  an opening at the one end of the storage portion that is in communication with the storage portion and through which the calculus is introduced into the storage portion, the other end of the storage portion being blocked; and
  an introducing portion configured to permit introduction of the retaining portion into the storage portion;

a shaft portion provided with a lumen configured to receive the retaining portion to permit the retaining portion to be introduced into the storage portion via the introducing portion; and a hand-operated unit that includes an operating member that is operable to control an introduction of the retaining portion into the storage portion, and wherein the retaining portion is configured to be inserted through an outer edge portion of the storage portion and fed into an interior open space of the storage portion and around calculi within the storage portion by operation of the operating member of the hand-operated unit.

2. The calculus removing device according to claim 1, wherein the collecting unit includes a through hole configured to communicate the lumen of the shaft portion with the storage portion.

3. The calculus removing device according to claim 2, wherein the retaining portion is one of a plurality of retaining portions, and the collecting unit includes a plurality of introducing portions each configured to permit introduction of a respective retaining portion into the storage portion.

4. The calculus removing device according to claim 3, wherein the plurality of introducing portions are spaced apart from each other on the storage portion in an axial direction from the opening toward a proximal end of the storage portion.

5. The calculus removing device according to claim 1, wherein the introducing portion is located at least in a vicinity of the opening.

6. The calculus removing device according to claim 1, wherein the collecting unit includes a first storage portion configured to store the calculus, and a second storage portion configured to receive and hold the first storage portion so that the first storage portion is mountable in and demountable from the second storage portion, the first storage portion being coupled to the shaft portion.

7. The calculus removing device according to claim 1, wherein the retaining portion to be introduced into the storage portion includes a linear member configured to be positioned in voids among the calculi by operation of the operating member.

8. The calculus removing device according to claim 1, wherein the retaining portion is one of a plurality of retaining portions, and the collecting unit includes a plurality of introducing portions each configured to permit introduction of a respective retaining portion into the storage portion.

9. The calculus removing device according to claim 8, wherein the plurality of introducing portions are spaced apart from each other on the storage portion in an axial direction from the opening toward a proximal end of the storage portion.

10. A calculus removing device comprising:
a retaining portion configured to retain calculus;
a calculus collection housing configured to be introduced into a living body, the calculus collection housing possessing oppositely located ends and an interior between the oppositely located ends that is configured to receive and store calculus collected from the living body, the oppositely located ends being a distal end and a proximal end, the calculus collection housing including an opening at the distal end which opens into the interior of the calculus collection housing and through which the calculus in the living body is introduced into the interior of the calculus collection housing;
a shaft portion connected to the calculus collection housing and projecting in a proximal direction away from the calculus collection housing;

a hand-operated unit connected to the shaft portion, at least a part of the retaining portion being located in the hand-operated unit;
a lumen extending through the shaft portion and communicating with both the interior of the calculus collection housing and the hand-operated unit;
the calculus collection housing being positionable in a ureter of a patient and being sized so that when the calculus collection housing, inclusive of the distal and proximal ends of the calculus collection housing, is positioned in the ureter, the shaft portion extends along at least a portion of the ureter of the patient, through a bladder of the patient, through a urethra of the patient and outside the patient; and
the hand-operated unit including an operating member that is operable to feed the retaining portion along the lumen and introduce the retaining portion into the interior of the calculus collection housing through an outer edge portion of the calculus collection housing into an interior open space of the calculus collection housing after the calculus is collected in the interior of the calculus collection housing to retain the calculus in the interior of the calculus collection housing, and wherein the retaining portion is configured to retain the calculus by being introduced into voids among calculi in the interior of the calculus collection housing.

11. The calculus removing device according to claim 10, wherein the lumen in the shaft portion communicates with the interior of the calculus collection housing by way of an introducing portion provided in the calculus collection housing, the introducing portion opening into the interior of the calculus collection housing.

12. The calculus removing device according to claim 10, wherein the retaining portion is one of a plurality of retaining portions, the calculus collection housing including a plurality of spaced apart introducing portions each opening into the interior of the calculus collection housing to permit a respective one of the retaining portions to be introduced into the calculus collection housing.

13. The calculus removing device according to claim 10, wherein the calculus collection housing is an inner cylinder, and further comprising an outer cylinder in which the inner cylinder is removably positioned.

14. The calculus removing device according to claim 10, wherein the retaining portion includes a wire configured to be positioned in the voids among calculi collected in the calculus collection housing through operation of the operating member.

15. A calculus removing device for removing calculus located in a living body, the calculus removing device comprising:
a calculus collection housing configured to be introduced into an ureter or a renal pelvis in the living body, the calculus collection housing possessing oppositely disposed distal and proximal ends between which is located an interior of the calculus collection housing, the distal end being an open distal end that opens into the interior of the calculus collection housing to permit the calculus in the living body to be introduced into the interior of the calculus collection housing;
a calculus retaining portion to retain calculus in the interior of the calculus collection housing, the calculus retaining portion configured to be inserted through an outer edge portion of the calculus collection housing into an interior open space of the calculus collection housing;

a shaft connected to the calculus collection housing and projecting in a proximal direction away from the calculus collection housing;

a lumen configured to receive the calculus retaining portion, the lumen extending throughout the shaft and possessing a distal-most end terminating at a through hole that is located in the interior of the calculus collection housing and that opens into the interior of the calculus collection housing; and a hand-operated unit comprised of an operating member that is operable to feed the calculus retaining portion along the lumen, to pass the calculus retaining portion through the through hole so that the calculus retaining portion is introduced into the interior of the calculus collection housing to retain the calculus that has been collected in the interior of the calculus collection housing, and wherein the calculus retaining portion is configured to retain the calculus by being introduced into voids among calculi within the calculus collection housing.

16. The calculus removing device according to claim 15, wherein the proximal end of the calculus collection housing is blocked.

17. The calculus removing device according to claim 16, wherein the calculus collection housing is positionable in a ureter of a patient and is sized so that when the calculus collection housing, inclusive of the distal and proximal ends of the calculus collection housing, is positioned in the ureter, the shaft portion extends along at least a portion of the ureter of the patient, through a bladder of the patient, through a urethra of the patient and outside the patient.

18. The calculus removing device according to claim 15, wherein the calculus collection housing is positionable in a ureter of a patient and is sized so that when the calculus collection housing, inclusive of the distal and proximal ends of the calculus collection housing, is positioned in the ureter, the shaft portion extends along at least a portion of the ureter of the patient, through a bladder of the patient, through a urethra of the patient and outside the patient.

* * * * *